United States Patent
Sage et al.

(10) Patent No.: US 9,227,926 B2
(45) Date of Patent: Jan. 5, 2016

(54) METHOD OF SYNTHESIS OF AZO COMPOUNDS

(71) Applicant: Arkema France, Colombes (FR)

(72) Inventors: Jean-Marc Sage, Oullins (FR); Jean-Michel Bossoutrot, Chaponost (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/321,189

(22) Filed: Jul. 1, 2014

(65) Prior Publication Data

US 2015/0011738 A1 Jan. 8, 2015

(30) Foreign Application Priority Data

Jul. 2, 2013 (FR) ...................... 13 56424

(51) Int. Cl.
*C09B 27/00* (2006.01)
*C07C 253/30* (2006.01)

(52) U.S. Cl.
CPC .................... *C07C 253/30* (2013.01)

(58) Field of Classification Search
CPC .... C07C 255/65; C07C 281/06; C09B 27/00; C09B 41/00; C09B 43/003
USPC ....................................................... 534/586
See application file for complete search history.

(56) References Cited

U.S. PATENT DOCUMENTS

| 2,469,358 A | 5/1949 | Alderson |
| 4,637,868 A | 1/1987 | Moroux |

FOREIGN PATENT DOCUMENTS

| CS | 232350 | 1/1985 |
| CS | 237123 | 7/1985 |
| CS | 239407 | 1/1986 |
| GB | 976552 | 11/1964 |
| JP | 52133924 | 11/1977 |
| JP | 52144622 | 12/1977 |
| RO | 90707 | 12/1986 |
| RO | 106881 | 7/1993 |
| RO | 106881 B1 * | 7/1993 |
| RO | 107406 | 11/1993 |
| WO | 2006067315 | 6/2006 |

OTHER PUBLICATIONS

Coll, Alberto Palomo "Oxidation Catalytic Systems. I.—Oxidation of Hydrazo Compounds" Research Department GEMA S.A., Affinity 42. May-Jun. 1985. pp. 312-314.*
Alberto Palomo Coll "Oxidation Catalytic Systems. I.—Oxidation of Hydrazo Compounds" Research Department GEMA S.A., Affinity 42. May-Jun. 1985. pp. 312-314.*
Drugs et al,. "Catalytic Oxidation of Hydrazo Derivatives Promoted by a TiCl3/HBr System," JACS Communications 2007, 129(45), 13784-13785.
English abstract of Palomo et al., Afinidad, 1985, 42(397), 312-314.
French Search Report dated Jan. 10, 2014 for French Application No. 1356424.

* cited by examiner

*Primary Examiner* — Nyeemah A Grazier
*Assistant Examiner* — Sagar Patel
(74) *Attorney, Agent, or Firm* — RatnerPrestia

(57) ABSTRACT

A process is provided for synthesizing an azo compound, such as AIBN, by oxidation of a hydrazo compound using hydrogen peroxide. This process comprises a step of adding to the reaction medium a particular reducing agent, such as hydrazine.

20 Claims, No Drawings

METHOD OF SYNTHESIS OF AZO COMPOUNDS

CROSS-REFERENCE TO RELATED APPLICATIONS

This application claims priority to French application 13.56424, filed Jul. 2, 2013, and incorporated herein by reference in its entirety for all purposes.

TECHNICAL FIELD

The present invention relates to a process for synthesizing an azo compound, such as azobisisobutyronitrile (AIBN or AZDN), by oxidation of a hydrazo compound using hydrogen peroxide. This process comprises a step of adding to the reaction medium a particular reducing agent, such as hydrazine.

BACKGROUND OF THE INVENTION

Azobisisobutyronitrile (or AIBN) is an azo compound that is commonly used in radical polymerization processes, as an initiator or catalyst. It is also known as a swelling agent for the manufacture of PVC foams or silicone seals.

AIBN is conventionally produced by converting acetone cyanohydrins into hydrazine, followed by oxidation with gaseous chlorine (U.S. Pat. No. 2,469,358; WO 2006/067 315). This process has also been applied to other azo compounds such as azodicarbonamide (GB 976 552). It has the major drawback, besides the intrinsic dangerousness of chlorine, of generating hydrochloric acid as a by-product, and as such the effluents, which are incidentally produced in large amounts, cannot be readily recycled. It is understood that the process with chlorine is therefore unsuited to the current environmental constraints.

To overcome this drawback, processes have been proposed for synthesizing azo compounds not using chlorine, but hydrogen peroxide as oxidizing agent. These processes require the presence of an activating agent, generally a bromine compound such as a bromide, or even an iodine derivative, used in acidic medium, in order for the reaction to be sufficiently fast and complete. Such processes have especially been described in documents U.S. Pat. No. 4,637,868; RO 90707; RO 107 406; RO 106 881. The reactivity of hydrogen peroxide, and thus the reaction yield, are generally improved by using metal catalysts in addition to the bromine or iodine compounds (Drug et al., JACS 2007, 129(45), 13784-13785; JP52-144622; JP52-133924), in particular catalysts based on molybdenum or tungsten (CS 237 123; CS 239 407; CS 232 350; Palomo et al., Afinidad, 1985, 42(397), 312-314) which have the advantage of being less toxic than tellurium, vanadium or selenium, for example.

Despite its undisputed advantages relative to the process with chlorine, the process with hydrogen peroxide, however, also itself generates effluents that are potentially hazardous to the environment, namely the mother liquors resulting from the filtration of the reaction medium to separate out the AIBN. These mother liquors in fact contain an appreciable amount of the catalyst and of the activators used. It has thus been suggested, not only for environmental reasons, but also to improve the economy of the process, to recycle these mother liquors into the reaction, optionally after concentration (CS 239 407; CS 237 123).

Unfortunately, it has been observed that in the presence of certain catalysts, the mother liquors are unstable over time and have a tendency to precipitate out, which is detrimental to their recycling or to their processing for the purpose of discharging into the environment. The present inventors have demonstrated that the addition of certain reducing agents to the reaction medium makes it possible to solve this problem.

A process is thus proposed for synthesizing azo compounds of high purity, with a yield of greater than 90%, allowing easy treatment of the effluents for the purpose of recycling them into the process and/or of discharging them into the environment, such that the economy of the process and its environmental impact are improved.

BRIEF SUMMARY OF THE INVENTION

One subject of the present invention is thus a process for synthesizing an azo compound, comprising the successive steps of:
a) reacting hydrogen peroxide with an aqueous solution of a hydrazo compound containing at least one organic or inorganic acid, at least one alkali metal bromide or hydrogen bromide and at least one water-soluble compound chosen from salts and acids based on a catalytic metal chosen from molybdenum and tungsten, so as to form a solution containing an azo compound,
b) adding the solution obtained in step (a) to at least one reducing agent chosen from hydrazine, sodium sulfite and sodium bisulfite, and mixtures thereof,
c) recovering all or part of the reaction mixture thus obtained,
d) separating the recovered reaction mixture into a fraction containing the azo compound and a mother liquor fraction, and
e) optionally, washing the fraction containing the azo compound to isolate it.

DETAILED DESCRIPTION OF EMBODIMENTS OF THE INVENTION

The process according to the invention comprises a first step, or step (a), of oxidation of a hydrazo compound, in aqueous solution, with hydrogen peroxide.

The hydrazo compound may be chosen from symmetrical hydrazo compounds bearing nitrogenous functions, in particular nitrile or amine functions, such as 2,2'-hydrazobisisobutyronitrile, 2,2'-hydrazobismethylbutyronitrile, 1,1'-hydrazobiscyclohexanecarbonitrile or 2,2'-hydrazodicarbonamide, preferably 2,2'-hydrazobisisobutyronitrile.

Besides the hydrazo compound, the aqueous solution may comprise at least one surfactant, especially a nonionic surfactant, in particular an alkyl sulfosuccinate such as bis(2-ethylhexyl)sulfosuccinate.

The pH of the aqueous solution is acidic and preferably between 0 and 2.

The hydrogen peroxide is generally introduced into the aqueous solution at a temperature of from 0 to 40° C., preferably from 0 to 20° C., for a period ranging from 2 to 6 hours. It is generally used in a slight molar excess relative to the hydrazo compound. The mole ratio of the hydrogen peroxide to the hydrazo compound is thus advantageously between 1:1 and 1.1:1 and preferably between 1.01:1 and 1.05:1, limits inclusive.

This oxidation reaction is performed in the presence of at least one catalyst, at least one activator and at least one acid, which are also present in the aqueous solution. The order of introduction of the various compounds into this solution is not critical, and the three abovementioned compounds may thus be added therein, followed by the hydrazo compound and finally the surfactant optionally used.

The catalyst comprises a water-soluble compound chosen from salts and acids based on a catalytic metal chosen from molybdenum and tungsten, preferably molybdenum. Examples of such water-soluble compounds are especially: alkali metal or ammonium salts of molybdenum, alkali metal or ammonium salts of tungsten, phosphomolybdic acid and alkali metal or ammonium salts thereof, phosphotungstic acid and alkali metal or ammonium salts thereof, and molybdosulfates, and mixtures thereof. Phosphomolybdic acid and the alkali metal or ammonium salts thereof, especially ammonium molybdate, are preferred.

The activator is an alkali metal bromide or hydrogen bromide. It may in particular be sodium bromide. It may be used in a mole ratio of the activator to the hydrazo compound ranging, for example, from 1:2 to 1:10 or even from 1:4 to 1:8.

As acid, any organic or inorganic acid may be chosen. However, it is preferable for the inorganic acid to be chosen from hydrochloric, sulfuric, hydrobromic and phosphoric acids, and mixtures thereof, preferably hydrochloric acid, and for the organic acid to be chosen from formic and acetic acids, and mixtures thereof. It may be used in a mole ratio of the acid to the hydrazo compound ranging, for example, from 1:1 to 1:5.

An aqueous solution is thus obtained containing an azo compound and a certain amount of catalytic metal and of hydrogen peroxide, especially. The second step, or step (b), of the process according to the invention comprises the addition, to this solution, of at least one reducing agent chosen from hydrazine, sodium sulfite and sodium bisulfite, and mixtures thereof. According to a preferred embodiment of the invention, the reducing agent is hydrazine in the case where the water-soluble compound is phosphomolybdic acid. Hydrazine has the advantage of forming only water and nitrogen gas in the effluents, and in the recycling loop of the process, and thus of not accumulating salts during the recycling. The reducing agent is generally used in an amount that is necessary and sufficient to neutralize the excess hydrogen peroxide measured after step (a) of the process.

A reaction mixture is thus obtained, which is then recovered totally or partially, for example to a proportion of from 30% to 60% by weight and especially from 45% to 55% by weight, in the third step, or step (c), of the process according to the invention.

The reaction mixture optionally not recovered may be recycled into step (a), whereas the recovered reaction mixture is separated, in a step (d), into a fraction containing the azo compound and a mother liquor fraction. The azo compound may be separated by filtration or centrifugation, preferably by centrifugation.

The fraction containing the azo compound may be washed one or more times with water, in a step (e), so as to recover an azo compound with a purity of greater than 90% and washing waters.

In a subsequent step (f) of the process, the mother liquor fraction may, for its part, be totally or partially recycled into step (a), it being understood that steps (a) to (f) are optionally repeated at least once, i.e. the mother liquor fraction may be recycled at least twice. In one variant of the process according to the invention, the mother liquor fraction may be concentrated, especially by distillation, before being recycled. The distillate obtained may then be readily treated, for example incinerated, in order to be discharged into the environment.

As indicated previously, the process according to the invention allows easy treatment of the effluents for the purpose of recycling them into the process and/or of treating them in order to discharge them into the environment. To this end, it may comprise an additional step of treating all or part of the mother liquor fraction produced in step (d) and/or of the washing waters produced in step (e) using an adsorbent, such as active charcoal, so as to retain the catalytic metal. The process according to the invention may also comprise a step of recovering the catalytic metal in aqueous solution form, by treating the adsorbent with a basic aqueous solution, especially of sodium hydroxide. It is preferred industrially to pass the mother liquor fraction and/or the washing waters to be treated through a column containing the adsorbent, for example in a granulated form, and then to recover the catalytic metal by passing a basic solution through this column, according to the well-known techniques for the use of these adsorbents.

The aqueous solution of catalytic metal may thus be recycled into step (a) of the process, optionally after concentration, whereas the mother liquors resulting from the filtration of the adsorbent and/or the washing waters from the adsorbent may be discharged into the environment. It has been demonstrated in the examples below that this variant of the invention makes it possible to recover and recycle an effective amount of catalyst, while at the same time discharging into the environment an effluent that is greatly depleted in catalyst.

The process according to the invention makes it possible to obtain in a reasonable time a high particle size of the azo compounds produced, typically in the region of 150 µm (as measured by laser scattering), which may prove to be advantageous in certain applications.

The invention will be understood more clearly in the light of the non-limiting examples that follow, which are given for purely illustrative purposes and are not intended to limit the scope of the invention, defined by the attached claims.

EXAMPLES

Reagents
In the examples that follow:
DHC denotes hydrazobisisobutyronitrile, a hydrazo compound obtained industrially by reacting acetone cyanhydrin with hydrazine hydrate, filtration and then washing with water, and stored in a refrigerator (T<10° C.). Its moisture content is 12.7% and its purity is greater than 99% by analysis.
The phosphomolybdic acid used is a product sold by the company Aldrich, which corresponds to the formula $H_3[P(Mo_3O_{10})_4] \cdot xH_2O$ and is used as supplied (molar mass 1825.25 g/mol in anhydrous form). The product used has a molybdenum content of 50%.
The ammonium molybdate is obtained from the company Aldrich and corresponds to the formula $H_{24}Mo_7N_6O_{24} \cdot 4H_2O$ with a molar mass of 1235.86 g/mol.
The sodium molybdate dihydrate is obtained from the company Aldrich, and corresponds to the formula $Na_2MoO_4 \cdot 2H_2O$ with a molar mass of 241.95 g/mol.
DOSS denotes bis(2-ethylhexyl) sulfosuccinate.
AZDN (or AIBN) denotes azobisisobutyronitrile.
Method for Sampling and Assaying the Residual Peroxide Content In the examples that follow, the residual peroxide contents are measured as follows. About 3-5 mL of the reaction mixture in suspension are taken and filtered so as to remove the solid AZDN and DHC present. About 1 gram of the filtered solution is weighed out and placed in a 250 mL flask, and 50 mL of distilled water, 15 mL of 30% by weight sulfuric acid and 15 mL of 30% KI solution are added. The flask is stoppered and then left in the dark for 15 minutes. The mixture is then titrated with a thiosulfate solution of normality 0.1 N up to disappearance of the yellow color. The hydrogen peroxide content is thus calculated:

$$\% \text{ residual } H_2O_2 = \frac{\text{volume in mL of } 0.1\ N \text{ thiosulfate}}{(2 \times 100 \times \text{mass of filtrate in grams})}$$

Method for Assaying the Residual Molybdenum

This is performed via the ICP (inductively-coupled plasma) technique.

Example 1

Combination of Reducing Agents with Phosphomolybdic Acid

A 1 liter glass reactor equipped with an anchor-type mechanical stirrer (stirring speed 500 rpm) is used. The reactor is equipped with a condenser. The hydrogen peroxide solution is introduced by means of a peristaltic pump via a flexible tube through the top of the reactor. The reactor is of jacketed type, cooled using a cryostat by circulation of cold water in the jacket.

The cryostat bath is set at 13° C. and is circulated on the reactor. 116.8 g of DHC (0.610 mol), 300 mL of water, 42.5 g of aqueous HCl solution containing 5 mol/L of HCl (0.18 mol), 10 g of sodium bromide (0.097 mol) and 2.4 g of phosphomolybdic acid are placed in the reactor. 0.1 g of DOSS is added and stirring is started. When the temperature of the reactor stabilizes (14° C.), the pump for introducing the hydrogen peroxide solution is switched on. 62.2 g of a 34.5% $H_2O_2$ solution, i.e. 0.630 mol, are introduced, at a constant rate, over a period of 4 hours. The temperature of the medium stabilizes at 16-17° C. during the addition of $H_2O_2$.

A sample is withdrawn at 1 hour of addition in order to check the consumption of the hydrogen peroxide introduced, and gives 0.18% of residual peroxide (if $H_2O_2$ were not consumed, about 1.4% of residual $H_2O_2$ solution would be obtained).

At the end of addition of $H_2O_2$, the reaction mixture is left stirring for a further 30 minutes. It is then noted that the medium develops an orange-yellow color typical of the formation of bromine. In parallel, the temperature of the medium redescends, indicating the end of reaction. An equivalent peroxide assay is then performed and indicates 0.18%, corresponding to the free bromine and to the residual peroxide equivalents.

The reaction mixture is then filtered through a sintered glass filter of porosity 4, and the mother liquors obtained, representing 402 g, are divided into 50 mL portions in glass flasks in order to perform the stability tests in the presence of the reducing agent. The flasks are stirred, and are then left to stand at room temperature (15-20° C.) for several days, in order to observe the formation of a deposit corresponding to the decomposition of the catalytic system. The results are collated in Table 1.

TABLE 1

| Reducing agent | 10% Hydrazine hydrate solution Ex1-a | 10% Hydrazine hydrate solution Ex1-b | NaHSO₃ Ex1-c |
|---|---|---|---|
| Addition | 1.15 g | 1.7 g | 0.45 g |
| Appearance 1 day | No deposit | No deposit | No deposit |
| Appearance 4 days | No deposit | No deposit | No deposit |
| Appearance 10 days | No deposit | No deposit | No deposit |

The AZDN obtained is washed twice with 300 g of water, and 102.5 g of AZDN containing 9.2% water, i.e. a yield of 95%, are obtained.

The solution of Example 1a stored for 10 days is subjected to centrifugation (800 rpm), which confirms the absence of deposit or of solids in suspension.

This example thus demonstrates the absence of precipitation of the mother liquors treated with the reducing agents according to the invention.

Example 2

Combination of a Reducing Agent with Ammonium Heptamolybdate

Example 1 is repeated using, instead of phosphomolybdic acid, the same amount of ammonium molybdate and, as reducing agent, NaHSO₃. It is noted that the solution obtained according to the invention does not have any deposit after 10 days.

Example 3 (Comparative)

Process Not Using Any Reducing Agent

The same reactions as described in Examples 1 and 2 are performed, but without, however, using any reducing agent. These tests are referred to, respectively, as Examples 3a and 3b.

It is observed in both cases that the filtration mother liquors are clear but lead, after 4 days or 10 days, respectively, to a yellow crystalline deposit in the bottom of the flask.

The presence of this deposit is confirmed by centrifugation, and demonstrates the absence of stability of the filtration mother liquors. Due to its insolubility in toluene and its color, this deposit cannot be AZDN and appears rather to correspond to crystals of molybdenum compound.

Example 4

Process Comprising a Step of Recycling of the Mother Liquors

The reactor described in Example 1 is used. The cryostat bath is set at 18° C. and circulated on the reactor. 116.8 g of DHC (0.610 mol), a solution comprising 335 mL of water, 6.5 g of HCl (0.18 mol), 10 g of sodium bromide (0.097 mol) and 2.4 g of phosphomolybdic acid are added to the reactor. 0.1 g of DOSS is added and stirring is started. After 10 to 15 minutes, the pump for introducing the hydrogen peroxide solution is switched on. 62.2 grams (0.63 mol) of an $H_2O_2$ solution containing 34.5% $H_2O_2$ are introduced via the peristaltic pump over a period of 4 hours.

During addition of $H_2O_2$, the temperature stabilizes at a value of about 22° C. A sample is taken at various times during the test in order to check the consumption of the hydrogen peroxide introduced. At the end of addition of the $H_2O_2$, the reaction mixture is left stirring for 2 hours. A dilute (10%) hydrazine hydrate solution is then added to neutralize the excess indicated by the peroxide assay.

The reaction mixture is then filtered through a sintered glass filter of porosity 4 and the mother liquors are collected separately. The crude AZDN obtained is washed four times with 200 g of water.

350 g of the collected mother liquors are reused in a new test with 116.8 g of DHC (0.61 mol) and with addition of 3.3 g of 36% HCl (0.033 mol), 2 g of NaBr (0.019 mol) and 0.48 g of phosphomolybdic acid, so as to conserve the initial concentrations of bromide, catalyst and acid. Three recycling operations are thus performed consecutively in sequence, keeping the same temperature, amount and rate of addition of $H_2O_2$ conditions, and also the same reaction time.

The results are collated in Table 2 below.

TABLE 2

| Ex. | Mass % residual $H_2O_2$ over time | | | | AZDN Purity mol % ($^1$H NMR) | Yield g/L (ICP) | Mo content g/L (ICP) |
| --- | --- | --- | --- | --- | --- | --- | --- |
| | 1 h | 2 h | 4 h | 6 h | | | |
| 4a | 0.42% | 1.04% | 0.17% | 0.18% | 99.7 | 95% | 2.77 |
| 4b | 0.99% | 1.70% | 0.10% | 0.09% | 99.7 | 97% | 2.7 |
| 4c | 0.95% | 1.50% | 0.12% | 0.15% | 99.7 | 96% | 2.65 |
| 4d | — | — | 0.13% | 0.13% | 99.7 | 95% | — |

This test demonstrates that the reactivity of the system stabilizes after one to two recyclings. The yield and purity of the AZDN obtained are moreover excellent.

Example 5

Process Comprising a Step of Adsorption of the Molybdenum Contained in the Mother Liquors The mother liquors, a strong blue in color, obtained in Example 4d are subjected to a test of molybdenum adsorption in the presence of active charcoal.

1.0 g or 0.5 g of powdered active charcoal (Norit® SX2 BET surface area 900 m²/g, d90 of 110 μm, commercially available) are added to 100 mL of mother liquors obtained in Example 4d and the whole is stirred at room temperature. The decolorization of the medium is noted over time by measuring the absorbance at a wavelength of 425 nm corresponding to an absorption band of the molybdenum blue complexes, using a Hach® DR 4000 machine equipped with a 10 mm square cuvette.

It is observed that active charcoal allows virtually quantitative adsorption of the molybdenum species present in the mother liquors.

Example 6

Process Comprising a Step of Adsorption and Recycling of Molybdenum

A test identical to that of Example 4a is reproduced. The mother liquors are combined with the AZDN washing waters and treated with 10 g of Norit® SX2 charcoal powder for 60 minutes with stirring at room temperature. The active charcoal is separated out by filtration and then retreated with 40 mL of 2% sodium hydroxide solution with stirring at room temperature. The charcoal is then rinsed with a further 60 mL of water, and about 100 mL of solution containing the recovered molybdenum catalyst are obtained. These 100 mL are reengaged in a reaction according to Example 4a instead of the 2.4 g of the phosphomolybdic acid catalyst, and the water added is adjusted to 235 mL to take into account the water supplied by the molybdenum catalyst solution engaged. After two hours of addition of $H_2O_2$, the content of residual assayed peroxide is 1.4%; it is 0.3% at 4 hours and it is 0.2% at the end (6 hours). Reactivity comparable to that of test 4b for which partial recycling of the mother liquors was performed with a supplement of phosphomolybdic acid catalyst is thus observed. The yield is 95%.

Example 7a

Process Comprising a Step of Adsorption of Molybdenum

The reactor described in Example 1 is used. The cryostat bath is set at 8° C. and circulated on the reactor. DHC (116.8 g, i.e. 0.610 mol), a solution comprising 335 mL of water, 6.5 g of HCl (0.18 mol), 20 g of sodium bromide (0.097 mol) and 3.7 g of sodium molybdate dihydrate are introduced into the reactor. 0.1 g of DOSS is added and stirring is started. After 10 to 15 minutes, the pump for introducing the hydrogen peroxide solution is switched on. 62.2 grams (0.63 mol) of an $H_2O_2$ solution containing 34.5% $H_2O_2$ are introduced via the peristaltic pump over 4 hours. The monitoring of the residual peroxide concentration during addition of the $H_2O_2$ shows that, under these conditions, the hydrogen peroxide is consumed gradually as it is added. At the end of addition, the reaction mixture is stirred for a further 15 minutes, and then 1 g of $NaHSO_3$ is added so as to neutralize the residual peroxide content. During the reaction, 13 mL of solution were taken for the purpose of analysis.

After filtering off the AZDN, the mother liquors, which contain 8.3 g/L of molybdenum (expressed as sodium molybdate dihydrate), are collected and the crude AZDN obtained (25% humidity), still containing 34 g of mother liquor, is washed with about 800 mL of water. 295 g of filtration mother liquors are stored for recycling into the following Example 7b. The remainder of the filtration mother liquors (104 g) is mixed with the AZDN waters derived from the washing which contain, by assay, 0.32 g/L of molybdate dihydrate. 962 g of solution containing 1.2 g/L of sodium molybdate dihydrate are obtained. This solution is treated for one hour with stirring at room temperature with 10 grams of Norit® SX2 charcoal powder. This solution is filtered. The filtered aqueous solution, which represents the effluent produced, is assayed at 0.08 g/L (i.e. 80 ppm) of sodium molybdate dihydrate.

This test shows that the treatment on active charcoal makes it possible to very substantially reduce the content of discharged molybdenum.

The active charcoal is recovered and resuspended in 10 mL of 4% sodium hydroxide, and then filtered and washed with 10 mL of water. This operation is repeated once. More than 80% of the molybdenum in the effluent is thus recovered.

The filtrates derived from the treatment with the sodium hydroxide solution and from the washing with water of the active charcoal are combined and this solution (40 g) is reused in the following Example 7b.

Example 7b

Process Comprising a Step of Recycling the Adsorbed Molybdenum

The cryostat bath of Example 1 is set at 8° C. and circulated on the reactor. 116.8 g of DHC (0.610 mol), 295 g of filtration mother liquors obtained in Example 7a, 40 g of the molybdate solution obtained at the end of Example 7a and 0.2 g of sodium molybdate dihydrate are introduced into the reactor so as to compensate for the losses arising from the samples taken for analysis and from the loss in the effluent after treatment with charcoal obtained in Example 7a. An addition of 6.8 g of 36% HCl (0.063 mol), 6.4 g of NaBr (0.067 mol) and 10 mL of water is performed so as to regain HCl and NaBr concentrations comparable to those of the test of Example 7a. 0.1 g of DOSS is added and stirring is started. After 10 to 15 minutes, the pump for introducing the hydrogen peroxide solution is switched on. 62.2 grams (0.63 mol) of a 34.5% $H_2O_2$ solution are introduced via the peristaltic pump over 4 hours. Monitoring of the residual peroxide concentration during the addition of the $H_2O_2$ shows that, under these conditions, hydrogen peroxide is consumed gradually as it is added, as in Example 7a. After filtration and washing of the AZDN, a yield of 97% is obtained.

Example 8a

Process Comprising a Step of Concentrating the Mother Liquors

The cryostat bath of Example 1 is set at 15° C. and circulated on the reactor. DHC (116.8 g, i.e. 0.610 mol), a solution comprising 335 mL of water, 6.5 g of HCl (0.18 mol), 10 g of sodium bromide (0.097 mol) and 2.4 g of ammonium heptamolybdate tetrahydrate are introduced into the reactor. 0.1 g of DOSS is added and stirring is started. After 10 to 15 minutes, the pump for introducing the hydrogen peroxide solution is switched on. 62.2 grams (0.63 mol) of a 34.5% $H_2O_2$ solution are introduced via the peristaltic pump over 4 hours. At the end of addition, the reaction mixture is stirred for a further 15 minutes, and 2 g of $NaHSO_3$ are then added so as to neutralize the residual peroxide content at the end of reaction (0.2%). The AZDN obtained is filtered off and then washed, and a yield of 95% is obtained.

360 g of mother liquors, derived from the filtration of the reaction medium after reaction, and thus representing 83% of the total amount of theoretical mother liquors after reaction, are subjected to concentration under a vacuum of 250 millibar at between 55 and 60° C. 295 g of concentrated solution are recovered, i.e. a 20% concentration of the solution, which corresponds practically to the water formed by the reaction and that provided by the hydrogen peroxide solution and the wet DHC. This concentrated solution containing the catalytic system may thus be reused (in Example 8b) as obtained, reengaging 83% of the initial amount of DHC and of $H_2O_2$ of the test, without addition of molybdate catalyst, bromide or acid.

Analyses of the DCO contained in the mother liquors before and after concentration show that, by this process, the level of DCO contained in the concentrated solution can be substantially reduced:

Mother liquors before concentration: DCO=8.9 g/L
Mother liquors after concentration by 20%, DCO=6.7 g/L
The distillate no longer containing any catalytic system (bromide, molybdenum) can be more easily discharged or treated by incineration.

Example 8b

Process Comprising a Step of Recycling of the Concentrated Mother Liquors

The cryostat bath of Example 1 is set at 15° C. and circulated on the reactor. DHC (96 g, i.e. 0.50 mol) and 295 g of concentrated mother liquors obtained in Example 8a are placed in the reactor. 0.1 g of DOSS is added and stirring is started. After 10 to 15 minutes, the pump for introducing the hydrogen peroxide solution is switched on. 51.5 grams (0.52 mol) of a 34.5% $H_2O_2$ solution are introduced via the peristaltic pump over 4 hours. Monitoring of the residual peroxide concentration during the addition shows that, under these conditions, the hydrogen peroxide is consumed gradually as it is added, as in Example 8a. It is thus observed that the catalytic system conserves its reactivity. After filtration and washing of the AZDN, a yield of 95% is obtained.

Example 9

Study of Stability of the Concentrated Mother Liquors

The cryostat bath of Example 1 is set at 7° C. and circulated on the reactor. 60 g of AZDN (0.304 mol), DHC (89.2 g, i.e. 0.469 mol), a solution comprising 335 mL of water, 6.5 g of HCl (0.18 mol), 20 g of sodium bromide (0.097 mol) and 3 g of phosphomolybdic acid are placed in the reactor. 0.1 g of DOSS is added and stirring is started. After 10 to 15 minutes, the pump for introducing the hydrogen peroxide solution is switched on. 47.6 grams (0.48 mol) of a 34.5% $H_2O_2$ solution are introduced via the peristaltic pump over 4 hours. Monitoring of the peroxides during the addition of the $H_2O_2$ shows that it is gradually consumed. At the end of addition, the reaction mixture is stirred for a further 15 minutes, and 2 mL of a 10% HHZ solution are then added in order to neutralize the residual peroxide content (0.1%) at the end of reaction. The AZDN obtained is filtered off and then washed, and a yield of 95% is obtained.

The recovered mother liquors are concentrated under 250 millibar at a temperature of 52-58° C. until 40 g of solution have been removed (concentration to 40%). A chromatographic analysis is performed on acetone, which is one of the main by-products contained in the mother liquors.

0.1% of acetone is assayed in the mother liquors before concentration. After concentration to 40%, no further trace of acetone is detected (less than 0.05%).

The mother liquors thus concentrated remain stable, without appearance of a precipitate or deposit, for more than 4 days and can be reused in reaction directly.

Example 10

Process Comprising a Step of Recycling of AZDN

Example 10-1

126 g of AZDN (0.78 mol), 631 g of water containing 12 g of HCl (0.33 mol), 19 g of NaBr (0.18 mol), 4.52 g of phosphomolybdic acid (Mo content of 50%, i.e. 0.023 mol of molybdenum) and 0.1 g of DOSS are placed in a 1.5 liter reactor equipped with a stirring system for blending a suspension. After switching on the stirrer and the jacketed cooling system, the temperature is allowed to stabilize at about 18° C.

78.05 g of 35% $H_2O_2$ (i.e. 0.80 mol of $H_2O_2$) are then added continuously over a period of 4 hours. During the reaction, the medium is maintained at a temperature of between 18 and 20° C. The reaction is stopped about 20 to 30 minutes after the end of introduction of $H_2O_2$. The end of reaction is visible by the formation of bromine and is monitored using a Pt redox probe (at the start of $H_2O_2$ introduction, the potential is about 500 mV, and at the end of reaction, the potential is about 800 mV).

An assay of the residual peroxides is performed and 4 mL of a 10% HHZ solution are added per 0.1% of $H_2O_2$ equivalent in solution.

All of the reactor suspension is then filtered. 245 g of AZDN (dry) are obtained, i.e. a yield of 95%. The filtration mother liquors are stored for partial recycling of the following test.

Examples 10-2 to 10-11

126 g (0.78 mol) of the AZDN obtained, 128 g of DHC (0.78 mol), 0.1 g of DOSS and 507.5 g of mother liquors derived from the filtration of the reaction medium during the preceding test are placed in the reactor of Example 10-1. 148 g of water containing 2.84 g of HCl, 6 g of NaBr and 1.45 g of phosphomolybdic acid are then added, so as to maintain a reaction medium of the same composition as that of example 10-1 (compensation for the losses due to the non-recycled part of the mother liquors, taking into account the dilution due to the supply of water by the reagents and the formation of water by the reaction).

The reaction is then performed as in Example 10-1, by continuously adding 78.05 g of 35% $H_2O_2$ over a period of 4 hours to the reaction medium maintained between 18 and 20° C.

The process is thus performed by recycling into test n+1 a part of the AZDN and of the mother liquors obtained in test n.

A particle size measurement is performed using a Masterziser® S machine. The measurement is performed on wet crystals using water as dispersant and a drop of Igepal® surfactant (ethoxylated nonylphenol), after 10 minutes of circulation in the measuring cell. The results are collated in Table 3 below.

TABLE 3

| Ex. | Particle size D10 (μm) | Particle size D50 (μm) | Particle size D90 (μm) |
|---|---|---|---|
| 10-2 | 46 | 110 | 193 |
| 10-3 | 44 | 111 | 200 |
| 10-4 | 49 | 114 | 208 |
| 10-5 | 58 | 126 | 224 |
| 10-6 | 68 | 140 | 241 |
| 10-7 | 65 | 152 | 262 |
| 10-8 | 51 | 148 | 275 |
| 10-9 | 55 | 147 | 280 |
| 10-10 | 55 | 137 | 270 |
| 10-11 | 57 | 138 | 265 |

It is seen that the mean particle size (D50) increases to stabilize after 5 recyclings at a value of 140-150 μm.

The purity of the AZDN produced was controlled on the fifth recycling (Example 10-6) and confirms that the process makes it possible to obtain a very pure product:

| Relative mol % | Example 10-6 |
|---|---|
| AZDN | 99.8 |
| DHC | 0.12 |
| Methacrylonitrile | 0.03 |
| Isobutyronitrile | 0.02 |

Example 11 (Comparative)

Process for Synthesizing AZDN by Oxidation with Chlorine

Example 11-1

128 g (0.78 mol) of DHC, 126 g of AZDN, 378 g of water, 425 g of an aqueous solution containing 13% HCl and 0.1 g of DOSS are successively added to the reactor of Example 10 equipped with a chlorine inlet at the bottom of the reactor. The stirrer and the cooling device (jacket) are switched on and the temperature is allowed to stabilize. 57 g of chlorine gas are then introduced continuously into the reaction medium over a total period of 4 hours. During the reaction, the reaction medium is maintained at a temperature of between 18 and 20° C. by adjusting, if necessary, the temperature of the cooling jacket. The reaction is stopped about 20 to 30 minutes after the end of introduction of the chlorine. The end of reaction may be monitored using a Pt redox probe. The excess chlorine not consumed leads to an increase of the redox potential, which rises from 200 mV to 800 mV at the end of the test.

The reactor suspension is then completely filtered to collect separately the AZDN and the reaction liquors. The filtered reaction liquors are recovered for recycling in the following test.

Example 11-2

126 g (0.78 mol) of the AZDN obtained in Example 11-1, 128 g of DHC (0.78 mol), 375 g of water, 0.1 g of DOSS and 425 g of mother liquors derived from the filtration of the reaction medium are placed in the reactor of Example 10.

The reaction is then performed as in Example 11-1, by introducing 57 g of chlorine gas into the reactor over 4 hours and maintaining the medium at between 18 and 20° C.

The process is thus performed by recycling into test n+1 a part of the AZDN and of the mother liquors obtained in test n, as described in example 11-2. It is observed that the particle size stabilizes after 5 to 8 recyclings at a mean D50 value of 100-110 μm, which is thus smaller than via the process engaging $H_2O_2$ as oxidizing agent.

What is claimed is:
1. A process for synthesizing an azo compound, comprising the successive steps of:
   a) reacting hydrogen peroxide with an aqueous solution of a hydrazo compound containing at least one organic or inorganic acid, at least one alkali metal bromide or hydrogen bromide, and at least one water-soluble compound selected from the group consisting of salts and acids based on a catalytic metal chosen from molybdenum and tungsten, so as to form a solution containing an azo compound;
   b) adding the solution obtained in step (a) to at least one reducing agent selected from the group consisting of hydrazine, sodium sulfite, sodium bisulfite, or mixtures thereof to obtain a reaction mixture;
   c) recovering all or part of the reaction mixture, wherein the part of the reaction mixture not recovered may be optionally recycled into step (a), to obtain a recovered reaction mixture;
   d) separating the recovered reaction mixture into a fraction containing the azo compound and a mother liquor fraction; and
   e) optionally, washing the fraction containing the azo compound to isolate the azo compound.

2. The process as claimed in claim 1, wherein the hydrazo compound is selected from symmetrical hydrazo compounds bearing nitrogenous functions.

3. The process as claimed in claim 1, wherein the aqueous solution contains an inorganic acid selected from the group consisting of hydrochloric, sulfuric, hydrobromic and phosphoric acids, or mixtures thereof.

4. The process as claimed in claim 1, wherein the aqueous solution contains an organic acid selected from the group consisting of formic and acetic acids, and mixtures thereof.

5. The process as claimed in claim 1, wherein the aqueous solution contains sodium bromide.

6. The process as claimed in claim 1, wherein the water-soluble compound is selected from the group consisting of a) alkali metal or ammonium salts of molybdenum and tungsten, b) phosphomolybdic acid, alkali metal salts thereof, or ammonium salts thereof, c) phosphotungstic acid, alkali metal salts thereof, or ammonium salts thereof, and d) molybdosulfates.

7. The process as claimed in claim 1, wherein the aqueous solution also contains at least one surfactant.

8. The process as claimed in claim 1, wherein the pH of the aqueous solution is between 0 and 2.

9. The process as claimed in claim 1, wherein the hydrogen peroxide is introduced into the aqueous solution at a temperature of from 0 to 40° C. for a period ranging from 2 to 6 hours.

10. The process as claimed in claim 1, wherein the reducing agent is hydrazine and the water-soluble compound is phosphomolybdic acid.

11. The process as claimed in claim 1, wherein the azo compound is separated out by filtration or centrifugation.

12. The process as claimed in claim 1, wherein the process additionally comprises a step (f) of recycling all or part of the mother liquor fraction into step (a), optionally after concentration of the mother liquor fraction, and wherein steps (a) to (f) are optionally repeated at least once.

13. The process as claimed in claim 1, wherein the process additionally comprises a step of treating all or part of the mother liquor fraction produced in step (d) using an adsorbent so as to retain the catalytic metal.

14. The process as claimed in claim 13, wherein the process additionally comprises a step of recovering the catalytic metal in aqueous solution form, by treating the absorbent using a basic aqueous solution.

15. The process as claimed in claim 14, wherein the process additionally comprises a step of recycling the aqueous solution of catalytic metal into step (a), optionally after concentration.

16. The process as claimed in claim 1, wherein in step (c) from 30% to 60% by weight of the reaction medium is recovered.

17. The process as claimed in claim 1, wherein the hydrazo compound is selected from the group consisting of 2,2'-hydrazobisisobutyronitrile, 2,2'-hydrazobismethylbutyronitrile, 1,1'-hydrazobiscyclohexanecarbonitrile and 2,2'-hydrazodicarbonamide.

18. The process as claimed in claim 1, wherein the aqueous solution contains hydrochloric acid.

19. The process as claimed in claim 1, wherein the aqueous solution comprises a phosphomolybdic acid, an alkali metal of phosphomolybdic acid, or an ammonium salt of phosphomolybdic acid.

20. The process as claimed in claim 1, wherein step e) is performed and yields washing waters and wherein the process includes an additional step of treating all or part of the washing waters using an adsorbent so as to retain the catalytic metal.

* * * * *